(12) United States Patent
Sculati

(10) Patent No.: US 6,997,904 B2
(45) Date of Patent: Feb. 14, 2006

(54) VISCOUS FLUID INJECTION SYSTEM

(76) Inventor: Robert David Sculati, Unit 6, 2140 Winston Park Dr., Oakville (CA) L6H 5V5

( * ) Notice: Subject to any disclaimer, the term of this patent is extended or adjusted under 35 U.S.C. 154(b) by 163 days.

(21) Appl. No.: 10/327,623

(22) Filed: Dec. 24, 2002

(65) Prior Publication Data

US 2004/0122367 A1  Jun. 24, 2004

(51) Int. Cl.
*A61M 37/00* (2006.01)

(52) U.S. Cl. .................. 604/140; 604/93.01

(58) Field of Classification Search ............... 604/131, 604/151, 140, 141, 143, 145, 146, 147, 93.01; 600/431, 432
See application file for complete search history.

(56) References Cited

U.S. PATENT DOCUMENTS

| | | | |
|---|---|---|---|
| 4,449,938 A | 5/1984 | Pollak | |
| 5,019,037 A | 5/1991 | Wang | |
| 5,033,656 A | 7/1991 | Bletter | |
| 6,077,247 A * | 6/2000 | Marshall et al. | ............ 604/156 |
| 6,123,685 A | 9/2000 | Reynolds | |
| 2002/0043539 A1 | 4/2002 | Pagel et al. | |

FOREIGN PATENT DOCUMENTS

| | | |
|---|---|---|
| EP | 0235905 A | 9/1987 |
| FR | 2193626 A | 2/1974 |

* cited by examiner

*Primary Examiner*—Kevin C. Sirmons
(74) *Attorney, Agent, or Firm*—Lynn Schumacher; Hill & Schumacher

(57) ABSTRACT

The present invention provides a fluid injection apparatus for injecting viscous fluids directly from a syringe in which it is commercially delivered. The fluid injection apparatus includes a cylindrical syringe sleeve into which the syringe is inserted from one end with a small hole at the other end of the sleeve through which the syringe needle or cannula protrudes. The apparatus includes a locking head assembly for retaining the syringe in the cylindrical syringe sleeve which includes a top plate and a locking flange which engages with the flange for locking the head assembly to the cylinder. The plunger in the syringe is discarded and when the locking head assembly is placed on the cylindrical syringe sleeve an internal flange with a gasket located on it is inserted into the top of the syringe chamber forming a seal. The head assembly includes a tube coupling for connecting a pressurizing gas such as air to the cylinder through the interior of the internal flange for pressurizing the syringe for expelling the viscous oil through the needle or cannula.

16 Claims, 4 Drawing Sheets

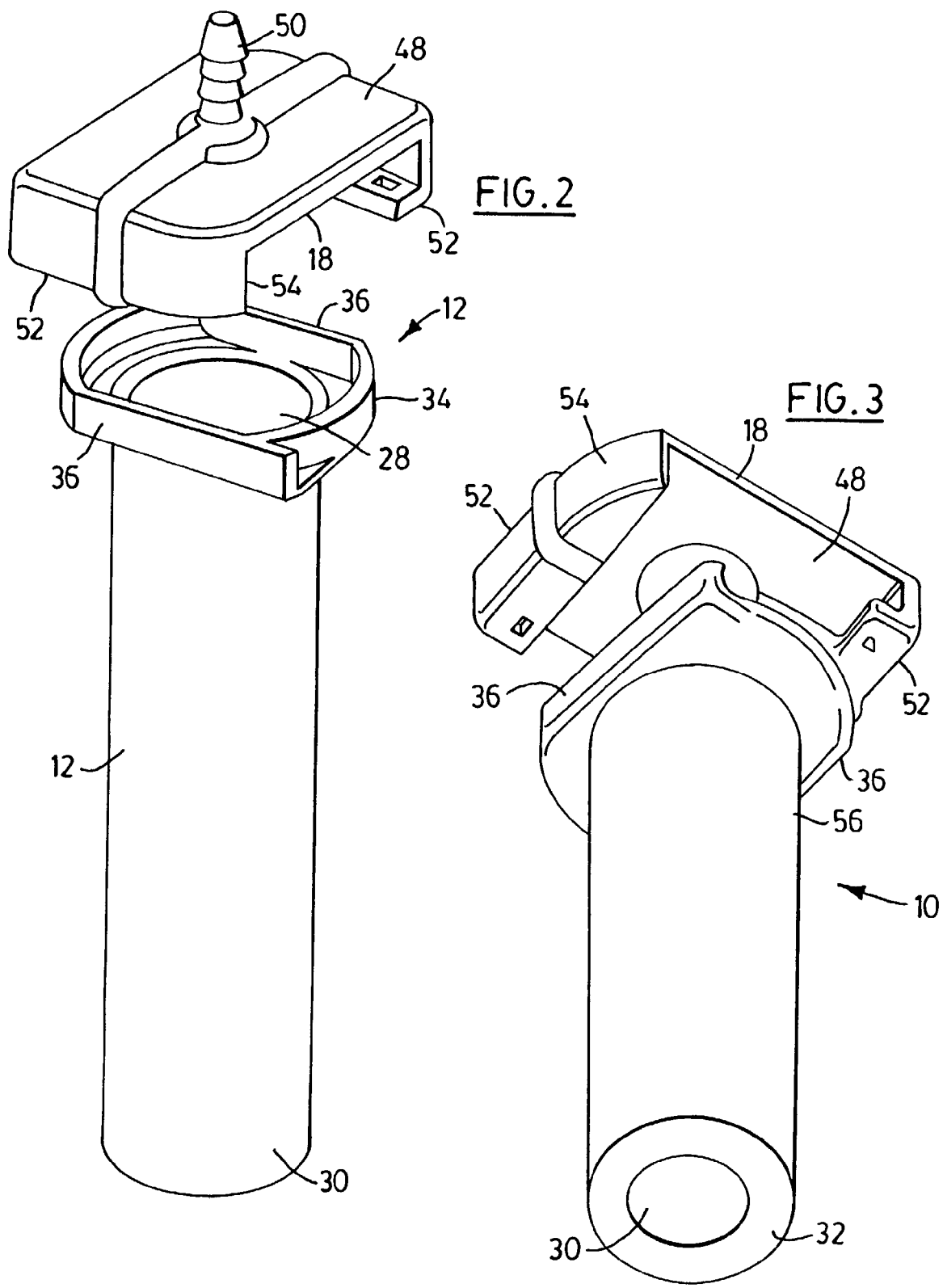

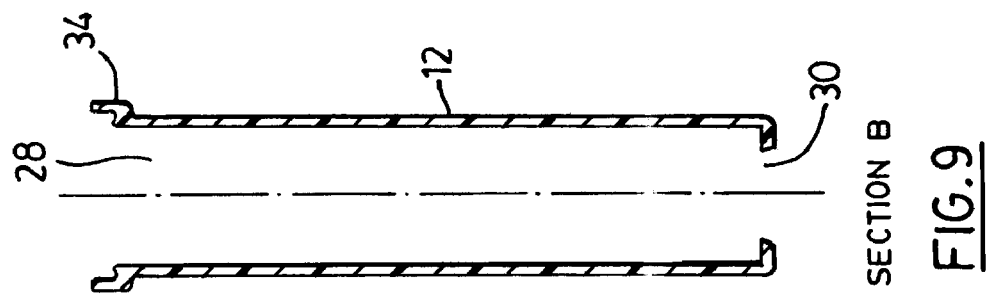
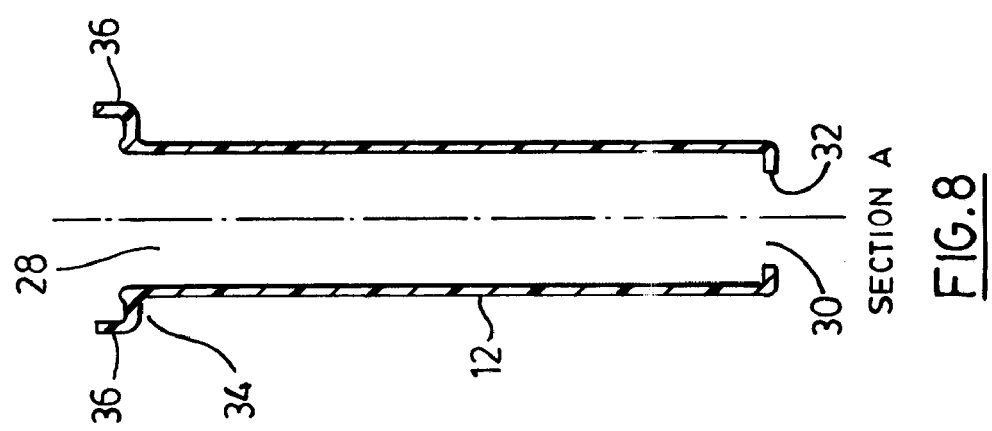
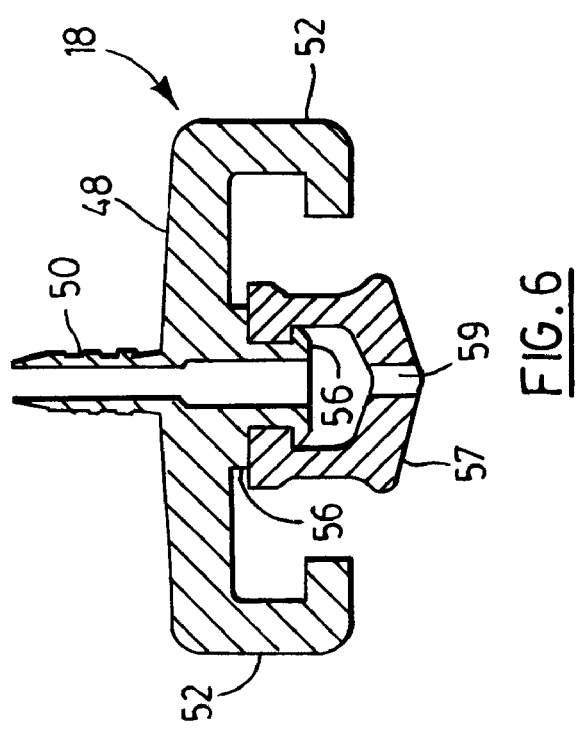
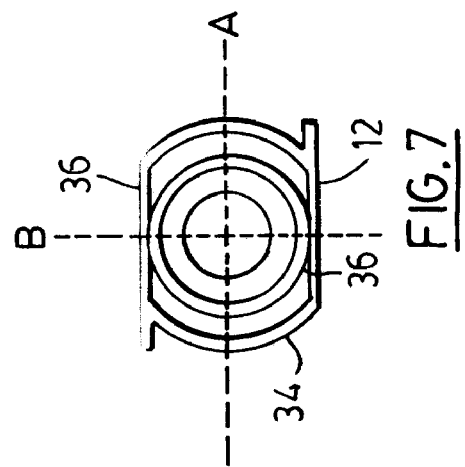

VISCOUS FLUID INJECTION SYSTEM

FIELD OF THE INVENTION

This invention relates generally to an apparatus for injecting viscous fluids including but not limited to silicone oil directly from the container, such as a disposable syringe, in which it is commercially delivered.

BACKGROUND OF THE INVENTION

Special high purity silicone oil has been developed as a medical device for use in the surgical treatment of the retina. Specifically, silicone oil is used as an internal tamponade in vitreoretinal surgery. It is indicated mainly for the surgical treatment of pathological changes generated by a proliferative process such as proliferative vitreoretinopathy (PVR), retinal detachment with PVR, giant retinal tears, and traction detachment associated with diabetic retinopathy.

In use, silicone oil is injected into the patient's eye during a surgical procedure. Silicone oil is a very viscous substance and it is commercially packaged in either sterile vials or disposable syringes. If the material is packaged in vials it must be dispensed into a syringe before it can be injected. The inherent high viscosity of silicone oil makes it physically difficult to inject the material from a hand held syringe through a small needle or cannula into the eye using a standard syringe with plunger.

In order to make the injection of the material easier, various mechanical devices have been developed to assist in the injection. Most of these devices utilize air pressure to push the plunger or stopper of a syringe. However, in order to use any of these devices the silicone oil must first be poured from the commercial container in which it is delivered into a syringe designed to fit the mechanical injection device. The pneumatic injection devices that have been developed to date, do not allow the user to inject the silicone oil or other viscous fluids directly from the syringe in which it is commercially delivered.

Therefore it would be very advantageous to provide a device for dispensing silicone oil or other viscous fluid which allows the user to inject the viscous material directly without the need to pour the fluid into a second container from the vial or syringe in which it is purchased into a new syringe designed to fit a mechanical injection device which overcomes this problem.

SUMMARY OF THE INVENTION

An objective of the present invention is to provide a device for injecting viscous fluids directly from the syringe, in which it is commercially delivered.

In one aspect of the invention there is provided a fluid injection apparatus for dispensing a viscous fluid for use with a disposable container which contains the viscous fluid therein, the disposable container including an outlet passageway for ejection of the viscous fluid therefrom, comprising;

a) a housing having first and second opposed ends and defining a chamber which is sufficiently large to receive therein said disposable container, said second opposed end having an opening sufficiently large for the outlet passageway to protrude therethrough and sufficiently small to retain the disposable container in said housing, said housing including a first locking flange located at said first opposed end; and b) a locking head assembly for locking the disposable container in said housing, said locking head assembly including a top plate and a second locking flange which engages with said first locking flange for locking said locking head assembly to said housing, said locking head assembly including a passageway in communication with an interior of said disposable container and coupling means for connecting a pressurizing fluid to said passageway for pressurizing the interior of the disposable container for expelling fluid therefrom, said coupling means including a rigid tube coupled to said top plate and extending through said top plate, and a flexible tube coupled to said rigid tube on a top side of said top plate for transmitting the pressurizing fluid into the interior of said disposable container, wherein said rigid tube defines a gasket retainer flange on a bottom side of said top plate, including a gasket mounted on said gasket retainer flange, said gasket having a sufficient size so that when said locking head assembly is coupled to said housing, said gasket is seated in the interior of said disposable container forming a seal so that said pressurizing fluid pressurizes the interior of the disposable container, and wherein said disposable container is a disposable syringe including a syringe cylinder containing said viscous fluid and said outlet passageway is defined by a syringe needle or cannula, and wherein when the disposable syringe is assembled within the housing and locking head assembly locked on the housing, the gasket is inserted and seated in a top portion of the syringe cylinder.

In another aspect of the invention there is provided a fluid injection kit for injecting viscous fluids, comprising;

a) a first housing defining a first chamber for holding a viscous fluid in an interior of said first chamber, said first housing have an outlet passageway for ejection of the fluid from the first chamber;

b) a second housing having first and second opposed ends and defining a second chamber being sufficiently large to receive therein said first housing, said second opposed end having an opening sufficiently large for the outlet passageway to protrude therethrough and sufficiently small to retain the first housing in said second housing, said second housing including a first flange at said first opposed end; and c) a locking head assembly for locking the second housing in said first housing, said locking head assembly including a top plate and a second locking flange which engages with said first locking flange for locking said locking head assembly to said first housing, said locking head assembly including a passageway in communication with said interior of said first chamber and coupling means for coupling a pressurizing fluid to said passageway for pressurizing said first chamber for expelling fluid therefrom, said coupling means including a rigid tube coupled to said top plate and extending therethrough, and a flexible tube coupled to said rigid tube on a top side of said top plate for transmitting the pressurizing fluid to an interior of said cylinder for forcing a liquid contained in said syringe out through the needle or cannula, wherein when assembled said locking head assembly is placed onto said first opposed end of said housing and said locking head assembly is rotated whereby said second locking flange rotates with respect to, and interlocks with, said first locking flange.

In a further aspect of the invention there is provided a fluid injection apparatus for dispensing a viscous fluid for use with a disposable container which contains the viscous fluid therein, the disposable container including an outlet passageway for ejection of the viscous fluid therefrom, comprising;

a) a housing having first and second opposed ends and defining a chamber which is sufficiently large to receive therein said disposable container, said second opposed end having an opening sufficiently large for the outlet passageway to protrude therethrough and sufficiently small to retain the disposable container in said housing, said housing including a first locking flange located at said first opposed end; and b) a locking head assembly for locking the disposable container in said housing, said locking head assembly including a top plate and a second locking flange which engages with said first locking flange for locking said locking head assembly to said housing, said locking head assembly including a passageway in communication with an interior of said disposable container and coupling means for connecting a pressurizing fluid to said passageway for pressurizing the interior of the disposable container for expelling fluid therefrom, said coupling means including a rigid tube coupled to said top plate and extending through said top plate, and a flexible tube coupled to said rigid tube on a top side of said top plate for transmitting the pressurizing fluid into the interior of said disposable container, wherein said rigid tube coupled to said top plate and extending through said top plate defines a gasket retainer flange on a bottom side of said top plate, including a gasket mounted on said gasket retainer flange, said gasket having a sufficient size so that when said locking head assembly is coupled to said housing, said gasket is seated in the interior of said disposable container forming a seal so that said pressurizing fluid pressurizes the interior of the disposable container, and wherein when assembled said locking head assembly is placed onto said first opposed end of said housing and said locking head assembly is rotated whereby said second locking flange rotates with respect to, and interlocks with, said first locking flange.

BRIEF DESCRIPTION OF THE DRAWINGS

Preferred embodiments of the invention will now be described, by way of example only, reference being had to the drawings, in which:

FIG. 2 shows a perspective view of a disassembled syringe sleeve and locking head assembly constructed in accordance with the present invention;

FIG. 3 shows another perspective view of the disassembled syringe sleeve and locking head assembly of FIG. 2 taken from another perspective; constructed in accordance with the present invention;

FIG. 6 is a cross sectional view of the locking head assembly of FIG. 5;

FIG. 7 shows a top view of the syringe sleeve and locking assembly;

FIG. 8 shows a view along line A of FIG. 7; and

FIG. 9 shows a view along line B of FIG. 7.

DETAILED DESCRIPTION OF THE INVENTION

Figure 1:
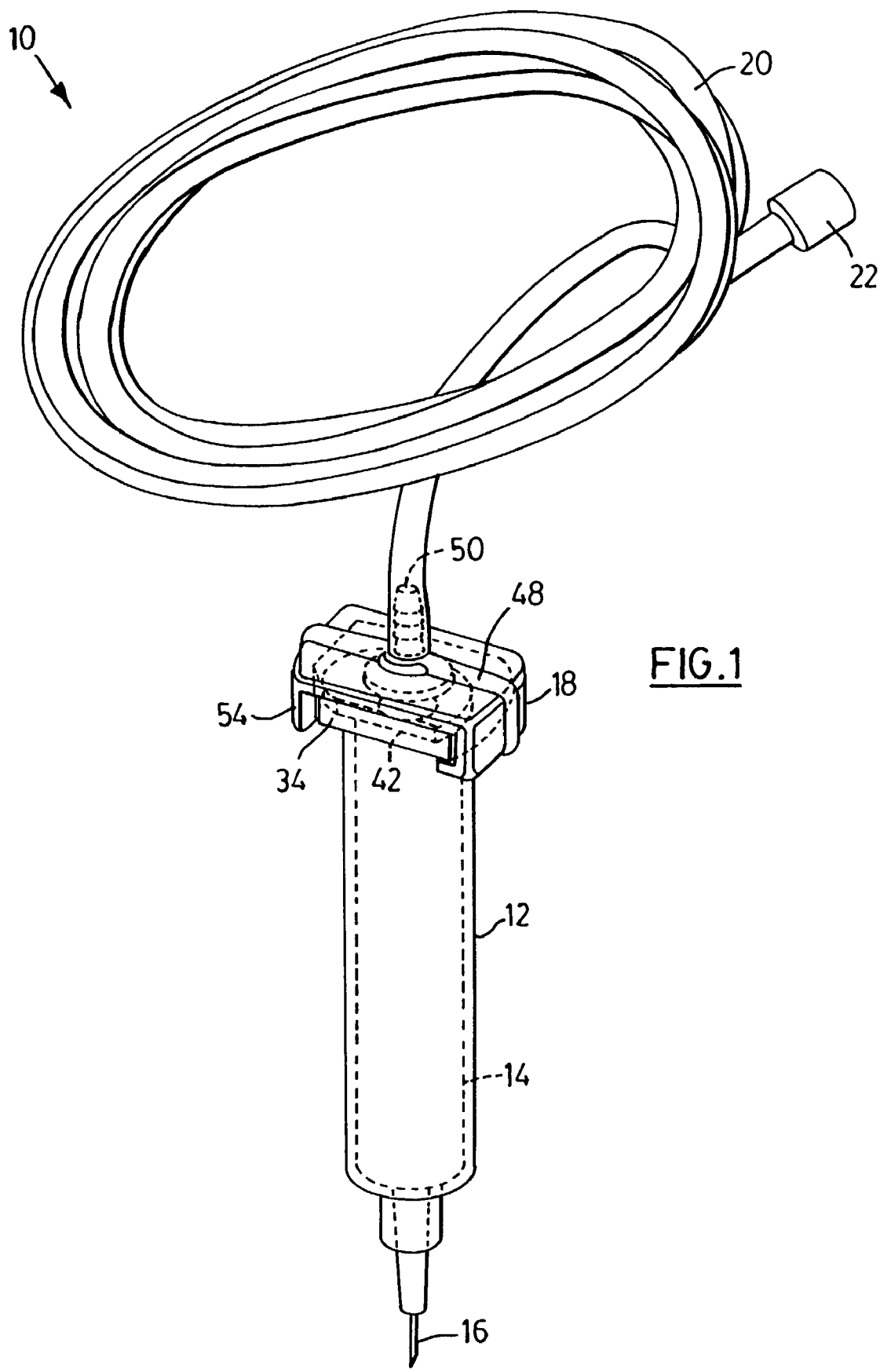
FIG. 1 shows an assembled syringe sleeve and locking head assembly containing a syringe constructed in accordance with the present invention.

Referring to FIG. 1, a perspective view of an assembled cylindrical sleeve and locking assembly is shown generally at 10 and includes a cylindrical sleeve 12 with a syringe 14 and associated needle or cannula 16 contained therein and a locking head 18 for locking syringe 14 into sleeve 12. A flexible tube 20 is attached at one end thereof to locking head 18 and the other end has a coupling 22 attached thereto for attachment of tube 20 to a pressurizing controller also known as a viscous fluid injection machine (not shown).

Figure 4:
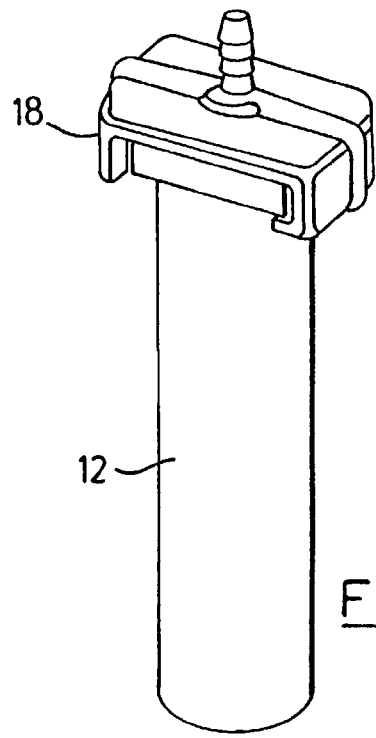
FIG. 4 is a perspective view showing the assembled syringe sleeve and locking head assembly of FIGS. 2 and 3.

With particular reference to FIGS. 2, 3 and 4, cylindrical sleeve 12 includes a hole 28 at one end of the cylindrical sleeve 12 large enough to receive syringe 14 (FIG. 1) inserted into sleeve 12 and a smaller hole 30 at the other end of the sleeve 12 defined by a circular inner edge 32 in which the end of the cylindrical body of syringe 14 fits with the needle or cannula 16 (FIG. 1) projecting through hole 30. Sleeve 12 includes an L-shaped flange 34 projecting outwardly at the other end of the cylinder 12 adjacent to hole 28 with flange 34 having two parallel edges 36, best seen in FIGS. 2 and 3. When syringe 14 is placed into sleeve 12, the top flange 42 of the syringe, shown in broken outline in FIG. 1, is cradled in flange 34.

Figure 5:
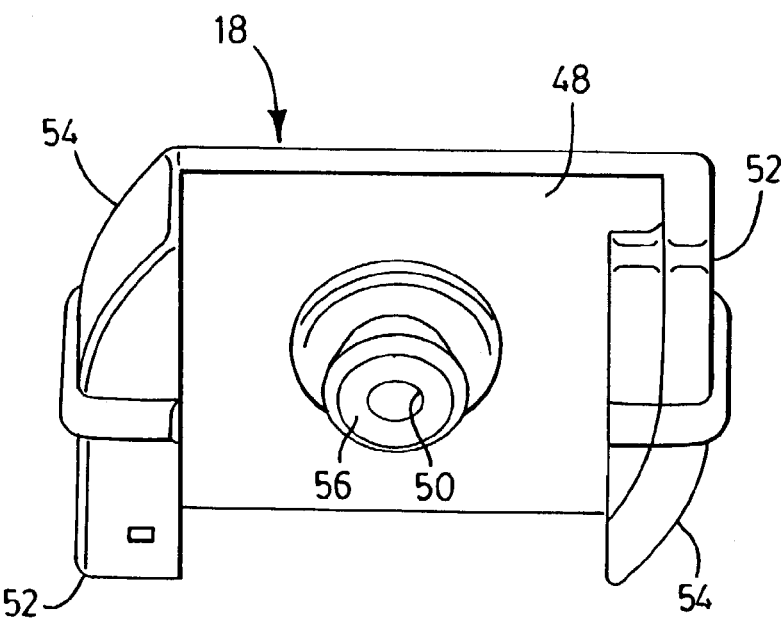
FIG. 5 is a perspective view of the locking head of FIGS. 2 to 4.

Locking head 18 includes a top plate 48 with a serrated tube coupling 50 projecting vertically upwardly from plate 48. Head 18 also includes two L-shaped brackets 52 descending from two opposed edges of plate 48 with each bracket having a rounded corner 54 so that the two rounded corners are diagonally disposed with respect to each other. Once syringe 14 is placed in sleeve 12 head 18 is lowered onto flange 34 with brackets 52 sliding down past planar sides 36 on flange 34. Locking head 18 is then rotated 90° which locks it in position on sleeve 14 (see FIG. 4), thereby locking the syringe 14 into the assembly as seen in FIG. 1. FIG. 5 shows a perspective view of the locking head 18 viewed from the bottom of top plate 45 and FIG. 6 shows a sectional view of the locking head. It can be seen from these Figures that the extension of tube 50 includes a gasket retaining flange 56 molded onto the extension of tube 50. When assembled, a flexible gasket (not shown) is placed on the end of tube 50 located below top plate 48 and is retained in place by retainer 56. The internal flange 56 is provided with the gasket 57 and is used to create the seal in the syringe cylindrical chamber. The hole 59 through gasket 57 is for the pressurizing fluid, preferably pressurized air, to access the interior of the container holding the viscous fluid. If the container containing the oil is a syringe, when assembling the device for injecting viscous fluids the syringe is put into the cylindrical sleeve 12, plunger is removed from the syringe chamber (not shown), and the locking head 18 is engaged with the flanges 52 and 54 on the locking head locking against flanges 36 on sleeve 12 so that the gasket 57 on flange 56 is inserted into the top of the syringe cylinder 14 forming a seal.

When the cylindrical sleeve 12 and locking head assembly 18 are assembled with the syringe 14 located in sleeve 12, the gasket fits into the open top of the syringe cylinder forming a leak tight joint. With the locking head 18 locked onto sleeve 12, the pressurizing fluid (preferably a gas such as air, nitrogen or other inert gas) is flowed from the controller (not shown) to which coupling 22 is attached, through flexible tube 20, through rigid tube 50 into the syringe 14 thereby pressurizing the syringe 14 to expel the heavy viscous silicone oil out through needle or cannula 16 (FIG. 1). As used herein, the phrase "coupling means" refers to rigid tube 50 and the flexible tube 20 attached thereto at one end, the other end being connected to the pressurizing means.

A significant advantage of the device disclosed herein is that it provides a device for injecting viscous fluids directly from the container, such as a syringe, in which it is commercially delivered. Particularly, purified silicone oil for eye operations and the like is commercially available from multiple manufacturers packaged in glass syringes produced by the Becton Dickinson Company and marketed by them as "Hypak" syringes. Another advantage of the device disclosed herein is that the commercially available glass syringe is encased in the plastic cylinder thus protecting the hands of the user from possible glass breakage which is particularly problematic when dispensing viscous fluids such as silicon oil since high pressures are needed which are dangerous when using glass syringes.

It will be understood that the device for injecting viscous fluids disclosed herein may be sold as a kit including sleeve 12 and associated locking head 18 along with the tubing 20 with or without the controller. Alternatively, the kit may also be sold with a "Hypak" syringe full of silicone oil and after use the entire kit may be discarded or recycled.

As used herein, the terms "comprises", "comprising", "includes" and "including" are to be construed as being inclusive and open ended, and not exclusive. Specifically, when used in this specification including claims, the terms "comprises", "comprising", "includes" and "including" and variations thereof mean the specified features, steps or components are included. These terms are not to be interpreted to exclude the presence of other features, steps or components.

The foregoing description of the preferred embodiments of the invention has been presented to illustrate the principles of the invention and not to limit the invention to the particular embodiment illustrated. It is intended that the scope of the invention be defined by all of the embodiments encompassed within the following claims and their equivalents.

Therefore what is claimed is:

1. A fluid injection apparatus for dispensing a viscous fluid for use with a disposable container which contains the viscous fluid therein, the disposable container including an outlet passageway for ejection of the viscous fluid therefrom, comprising;
  a) a housing having first and second opposed ends and defining a chamber which is sufficiently large to receive therein said disposable container, said second opposed end having an opening sufficiently large for the outlet passageway to protrude therethrough and sufficiently small to retain the disposable container in said housing, said housing including a first locking flange located at said first opposed end; and
  b) a locking head assembly for locking the disposable container in said housing, said locking head assembly including a top plate and a second locking flange which engages with said first locking flange for locking said locking head assembly to said housing, said locking head assembly including a passageway in communication with an interior of said disposable container and coupling means for connecting a pressurizing fluid to said passageway for pressurizing the interior of the disposable container for expelling fluid therefrom, said coupling means including a rigid tube coupled to said top plate and extending through said top plate, and a flexible tube coupled to said rigid tube on a top side of said top plate for transmitting the pressurizing fluid into the interior of said disposable container, wherein said rigid tube defines a gasket retainer flange on a bottom side of said top plate, including a gasket mounted on said gasket retainer flange, said gasket having a sufficient size so that when said locking head assembly is coupled to said housing, said gasket is seated in the interior of said disposable container forming a seal so that said pressurizing fluid pressurizes the interior of the disposable container, and wherein said disposable container is a disposable syringe including a syringe cylinder containing said viscous fluid and said outlet passageway is defined by a syringe needle or cannula, and wherein when the disposable syringe is assembled within the housing and locking head assembly locked on the housing, the gasket is inserted and seated in a top portion of the syringe cylinder.

2. The apparatus according to claim 1 wherein said housing includes a cylinder with said first opposed end having an opening sufficiently large to receive therein the syringe cylinder and the second opposed end having an opening sufficiently large for a needle or cannula to protrude therethrough and sufficiently small to retain therein a cylindrical syringe body including the viscous fluid.

3. The apparatus according to claim 1 wherein said pressurizing fluid is a chemically inert gas.

4. The apparatus according to claim 3 wherein said inert gas is air.

5. The apparatus according to claim 1 wherein said housing and said locking head assembly are produced from a plastic material.

6. The apparatus according to claim 5 wherein said housing is produced from a substantially clear plastic material.

7. A fluid injection apparatus for dispensing a viscous fluid for use with a disposable container which contains the viscous fluid therein, the disposable container including an outlet passageway for ejection of the viscous fluid therefrom, comprising:
  a) a housing having first and second opposed ends and defining a chamber which is sufficiently large to receive therein said disposable container, said second opposed end having an opening sufficiently large for the outlet passageway to protrude therethrough and sufficiently small to retain the disposable container in said housing, said housing including a first locking flange located at said first opposed end; and
  b) a locking head assembly for locking the disposable container in said housing, said locking head assembly including a top plate and a second locking flange which engages with said first locking flange for locking said locking head assembly to said housing, said locking head assembly including a passageway in communication with an interior of said disposable container and coupling means for connecting a pressurizing fluid to said passageway for pressurizing the interior of the disposable container for expelling fluid therefrom, said coupling means including a rigid tube coupled to said top plate and extending through said top plate, and a flexible tube coupled to said rigid tube on a top side of said top plate for transmitting the pressurizing fluid into the interior of said disposable container, wherein said rigid tube coupled to said top plate and extending through said top plate defines a gasket retainer flange on a bottom side of said top plate, including a gasket mounted on said gasket retainer flange, said gasket having a sufficient size so that when said locking head assembly is coupled to said housing, said gasket is seated in the interior of said disposable container forming a seal so that said pressurizing fluid pressurizes the interior of the disposable container, and wherein when assembled said locking head assembly is placed onto said first opposed end of said housing and said locking head assembly is rotated whereby said second locking flange rotates with respect to, and interlocks with, said first locking flange.

8. A fluid injection kit for injecting viscous fluids, comprising;
   a) a first housing defining a first chamber for holding a viscous fluid in an interior of said first chamber, said first housing have an outlet passageway for ejection of the fluid from the first chamber;
   b) a second housing having first and second opposed ends and defining a second chamber being sufficiently large to receive therein said first housing, said second opposed end having an opening sufficiently large for the outlet passageway to protrude therethrough and sufficiently small to retain the first housing in said second housing, said second housing including a first flange at said first opposed end; and
   c) a locking head assembly for locking the second housing in said first housing, said locking head assembly including a top plate and a second locking flange which engages with said first locking flange for locking said locking head assembly to said first housing, said locking head assembly including a passageway in communication with said interior of said first chamber and coupling means for coupling a pressurizing fluid to said passageway for pressurizing said first chamber for expelling fluid therefrom, said coupling means including a rigid tube coupled to said top plate and extending therethrough, and a flexible tube coupled to said rigid tube on a top side of said top plate for transmitting the pressurizing fluid to an interior of said cylinder for forcing a liquid contained in said syringe out through the needle or cannula, wherein when assembled said locking head assembly is placed onto said first opposed end of said housing and said locking head assembly is rotated whereby said second locking flange rotates with respect to, and interlocks with, said first locking flange.

9. The fluid injection kit according to claim 8 wherein said rigid tube coupled to said top plate and extending through said top plate defines a gasket retainer flange on a bottom side of said top plate, including a gasket mounted on said gasket retainer flange, said gasket having a sufficient size so that when said locking head assembly is coupled to said second housing, said gasket is seated in the interior of said disposable container forming a seal so that said pressurizing fluid pressurizes the interior of the disposable container.

10. The fluid injection kit according to claim 8 herein said first housing is a disposable syringe containing a viscous fluid and said outlet passageway is defined by a syringe needle or cannula.

11. The fluid injection kit according to claim 8 wherein said viscous fluid is high purity silicone oil.

12. The fluid injection kit according to claim 8 wherein said second housing includes a cylindrical sleeve having a diameter large enough so that said disposable syringe slides into said cylindrical sleeve.

13. The fluid injection kit according to claim 8 wherein said pressurizing fluid is a gas.

14. The fluid injection kit according to claim 13 wherein said pressurizing gas is air.

15. The fluid injection kit according to claim 8 wherein said housing and said locking head assembly are produced from a plastic material.

16. The fluid injection kit according to claim 15 wherein said housing is produced from a substantially clear plastic material.

* * * * *